United States Patent

Suda et al.

[11] 3,956,385
[45] May 11, 1976

[54] PROCESS FOR PRODUCING SULFONYLAMIDES

[75] Inventors: Hideaki Suda, Takai; Tatsuo Kanda; Hiroshige Tomita, both of Toyonaka; Hirotoshi Nakanishi; Hiromu Hida, both of Minoo; Tatsumi Nuno, Toyonaka; Seiichi Akutsu; Masayuki Maeyashiki, both of Kakogawa, all of Japan

[73] Assignee: Sumitomo Chemical Company, Limited, Osaka, Japan

[22] Filed: Apr. 16, 1974

[21] Appl. No.: 461,445

[30] Foreign Application Priority Data
Apr. 18, 1973  Japan.............................. 48-44410
June 15, 1973  Japan.............................. 48-68138

[52] U.S. Cl. .................. 260/556 A; 260/556 AR; 260/556 F; 260/583 G; 260/556 R
[51] Int. Cl.² .............. C07C 143/72; C07C 143/84
[58] Field of Search...... 260/556 A, 556 AR, 556 F, 260/556 R, 583 G

[56] References Cited
UNITED STATES PATENTS
2,136,171  11/1938  Maier.............................. 260/583 G
2,163,181  6/1939   Ulrich et al..................... 260/583 G
2,225,960  12/1940  Orthner et al................. 260/556 A
3,153,096  10/1964  Soenksen et al............. 260/583 G
3,238,258  3/1966   Daemker....................... 260/556 A OTHER PUBLICATIONS
Kirk–Othmer Encyclopedia of Chemical Technology Vol. 19 (1970), pp. 252–258.

Primary Examiner—Arthur P. Demers
Attorney, Agent, or Firm—Wenderoth, Lind & Ponack

[57] ABSTRACT

Sulfonylamide derivatives of the formula,

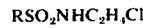

wherein R is an alkyl or a phenyl group, which are particularly useful for the production of photographic chemicals, are prepared by the reaction between a sulfonylhalide of the formula,

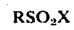

wherein R is as defined above, and X is chlorine or bromine, and 2-chloroethylamine or its salt, which is prepared by the chlorination of monoethanolamine with thionylchloride.

10 Claims, No Drawings

PROCESS FOR PRODUCING SULFONYLAMIDES

The present invention relates to a method for preparing sulfonylamide derivatives of the formula (I), $$RSO_2NHC_2H_4-Cl \qquad (I)$$

wherein R is a $C_1 - C_6$ alkyl group or a phenyl group which may be substituted, which sulfonylamide derivatives are very important intermediates widely used for medicines, pesticides, dyestuffs and photographic chemicals. The compounds have a highly active chlorine atom at the 2-position thereof, so that they are recently being used in a large amount as an alkylating agent which exhibits a unique activity, as well known, for example, in Japanese Layed Open Patent (unexamined) No. 17724/1972. The homologs are also widely used as disclosed in German Pat. No. 1,081,311 and Belgian Pat. No. 569,130.

The typical, well-known method for preparing the sulfonylamides is one including the reaction between sulfonylchloride and ethylene imine as described in Am. 566, 210–244, (1950).

The method, however, has many problems in the industrial application, in terms of working environment and economy, because ethyleneimine is highly toxic and because the reaction yield is so low as below 55 %. Further disadvantageously, as for this method including the use of methanol as a solvent, the use of methanol is considered to be very undesirable because of the coexistence of methanol having an active hydrogen atom and the highly active compounds of the formula (I) and sulfonylchloride.

Preparation of homologs of the present compounds, for example 2-bromoethylmethanesulfonylamide, is described in the above mentioned German Pat. No. 1,081,311 and Belgian Pat. No. 569,130, in which pyridine is used as a solvent and base, and yield is not shown. The preparation is treaced by the inventors with only 50 % of yield, and therefore it is not satisfactory for industrial production in terms of materials and yield.

Next, salts of 2-chloroethylamine, for example hydrochloride thereof, which are a material used according to the present invention have so far been prepared by chlorination of ethanolamine with a chlorinating agent, and typical processes are (1) a process using hydrogen chloride and (2) a process using thionylchloride. As is well known, however, the process (1) needs relatively high-priced hydrogen chloride and a high temperature and a high pressure and produces water as a by-product thereby making difficult selection of a material of reaction vessel and making the product very expensive. With the process (2), on the other hand, the chlorination itself proceeds under a mild condition with a relatively high yield, however the process has serious problems in terms of treatment of hydrogen chloride as a by-product, separation of the resulting 2-chloroethylamine hydrochloride, and difficulty of direct use of the separated salt in the subsequent reaction step.

From the situation above mentioned, the inventors have studied the preparation of sulfonylamides of the formula (I), and found a very advantageous method which can easily give the desired product in a high yield and a high purity without defects of the conventional processes.

The present invention provides a method for preparing a sulfonylamide of the formula (I), $$R-SO_2NHC_2H_4-Cl \qquad (I)$$

wherein R is a $C_1 - C_6$ alkyl or a substituted or unsubstituted phenyl group, which comprises reacting sulfonylhalide of the formula (II), $$R-SO_2-X \qquad (II)$$

wherein R is the same as defined above, and X is a chlorine or bromine atom, with 2-chloroethylamine or a salt thereof in the presence of a base.

More specifically, the invention provides a method for preparing the sulfonylamide of the formula (I), which comprises (1) chlorinating monoethanolamine hydrochloride with thionyl chloride in a water-insoluble solvent, (2) recovering the resulting 2-chloroethylamine hydrochloride in the form of aqueous solution by extracting the 2-chloroethylamine hydrochloride with water or by distillating a mixture of water and the chlorination mixture, and (3) reacting the aqueous solution of 2-chloroethylamine hydrochloride with the sulfonylhalide of the formula (II) in the presence of a base.

Still more specifically, the invention provides a method for preparing the sulfonylamide of the formula (I), which comprises (1) forming monoethanolamine hydrochloride by contacting monoethanolamine with hydrogen chloride or hydrochloric acid, (2) chlorinating the resulting monoethanolamine hydrochloride with thionyl chloride in a water-insoluble solvent, a sulfur-dioxide-containing hydrogen chloride by-produced in the chlorination (2) being recycled to the formation of monoethanolamine hydrochloride (1) in the presence of water, (3) recovering the resulting 2-chloroethylamine hydrochloride in the form of aqueous solution either by extracting the 2-chloroethylamine hydrochloride with water and removing the by-produced sulfur dioxide remaining in the resulting aqueous solution, or by distillating a mixture of the chlorination mixture with water, and (4) reacting the resulting aqueous solution of 2-chloroethylamine hydrochloride with the sulfonylhalide of the formula (II) in the presence of a base.

According to the present invention, the desired products can be obtained in a high yield and a high purity without all the disadvantages in material and yield which are accompanied by the conventional methods.

Examples of the group represented by R include a methyl, ethyl, n- or iso-propyl, butyl, hexyl, octyl or cyclohexyl group, or a phenyl group which may be substituted by a halogen atom or a $C_1 - C_6$ alkyl, $C_1 - C_3$ alkoxy, acetyl, $C_1 - C_2$ acylamino, $C_1 - C_2$ alkylamino or nitro group.

The salt of 2-chloroethylamine includes, for example its sulfate, hydrochloride, hydrobromide and acetate, among which 2-chloroethylamine hydrochloride is preferably used.

The bases which are used according to the present invention include alkali hydroxides, alkali carbonates and bicarbonates, and 2-chloroethylamine itself, which are generally used in an aqueous solution thereof.

With the proportion of materials which is used according to the present invention, 2-chloroethylamine or its salt is used in an about equimolar amount to the sulfonylhalide of the formula (II), or in about two moles per mole of the sulfonylhalide, when used as the base. The ratio by chemical equivalent of the 2-chloroethylamine or its salt to the base is about 1:1 to 2.

When the bases are used in an aqueous solution thereof, their concentration may arbitrarily be determined, however with the total amount of water, it is desirable that the amount is a little more than that required to saturate with an inorganic salt resulting from the reaction, for example when the resulting salt is sodium chloride, the total amount of water used in preferably such that a 15 to 25 % aqueous sodium chloride solution can be formed.

According to the present invention, inert solvents may be used, in addition to the above-mentioned amount of water, in the amount of 1 to 20 times based on the total weight of sulfonylhalides and 2-chloroethylamine or its salt.

The reaction temperatures which are used according to the present invention are 0° to 80°C., preferably 0° to 50°C. And values of pH are 5 to 10, preferably 6 to 9.

Under the above conditions, the reaction proceeds smoothly. After the reaction is over, in most cases, the solution of the desired products is separated from the reaction mixture, and evaporation of the solvent gives the desired product. The product has a high purity as it is, for example above 98 %, and can be used without problems for the subsequent reaction step for the preparation of medicines, pesticides, dyestuffs and photographic chemicals.

The amidation between the sulfonylhalide and 2-choroethylamine or its salt for preparing sulfonylamides of the present invention can very remarkably be improved by using halogenated hydrocarbons as a solvent for reaction and/or for extraction. Although the amidation can be carried out with the use of usual inert solvents, the use of such solvents as usual hydrocarbon type or ether type solvents, is not always desirable in respect with operation and yield.

From the situation as above mentioned, the inventors have extensively studied a new preparation of sulfonylamides of the formula (I), and found that aliphatic or aromatic halogenated hydrocarbons are favorably used as a solvent to carry out the reaction between compounds of the formula (II) and 2-chloroethylamine or salts thereof with a great ease and a high yield in the presence of bases, and further found that the said solvents are very suitable not only for the amidation reaction but also for extraction of the desired products.

The aliphatic or aromatic halogenated hydrocarbons include chloroform, carbontetrachloride, 1,2-dichloroethane, 1,1,2-trichloroethane, 1,1,2,2-tetrachloroethane, 1,2-dichloroethylene, 1,1,2-trichloroethylene, 1,1,2,2-tetra-chloroethylene, n-propylchloride, 1,2-difluoro-1,1,2,2-tetra-chloroethane, monochlorobenzene, 0-dichlorobenzene, mixed dichlorobenzene and fluorobenzene, among which chloroform and 1,2-dichloroethane are particularly preferred.

The amount of the solvent used is about 1 to 20 times by weight based on the total weight of sulfonylhalides (II) and 2-chloroethylamine or salts thereof.

In the present invention, when the reaction is carried out with solvents other than the solvents above specified, for example the usual solvents such as benzene, toluene, ethylacetate, isobutylalcohol, methylisobutyl ketone, hexane and diethylether, or without solvents, sulfonylhalides or the resulting compounds of the formula (I) are liable to be decomposed, resulting in a decrease of yield.

As mentioned above, the solvents above specified is much suitable as a solvent for extraction, so that the desired product can easily be obtained by separating the solvent layer containing the desired product from the aqueous layer and by removing the solvent by distillation.

Next, the preparation of 2-chloroethylamine hydrochloride by chlorinating monoethanolamine hydrochloride with thionylchloride will be illustrated as follows.

The reaction between monoethanolamine hydrochloride and thionylchloride is carried out in a molar ratio of 1:1.05 – 1.2, at 50° to 100°C. for 3 to 10 hours, in water-insoluble solvents such as benzene, toluene, xylene, monochlorobenzene, dichlorobenzene and 1,2-dichloroethane, and in the presence of a catalyst such as dimethylformamide, diethylformamide, N-methylpyrrolidone and pyridine to obtain 2-chloroethylamine hydrochloride with good purity. And, as a result of further investigation, the inventors have found that sulfur dioxide which is produced as a by-product in the course of the chlorination acts as a negative catalyst in the subsequent amidation, i.e. the reaction between the sulfonylhalide (II) and the resulting 2-chloroethylamine or salts thereof, and that the yield can be much increased by forcing sulfur dioxide to be removed.

Furthermore, the inventors have found that the amidation is disadvantageously affected not only in the system containing by-produced sulfur dioxide, but also in the system contaminated afterwards with sulfur dioxide, sulfites such as sodium sulfite and sodium hydrogen sulfite, and that, also in the latter case, removal of sulfur dioxide and the sulfites can give a very high yield.

Sulfur dioxide in the system containing 2-chloroethylamine hydrochloride can be removed by heating the system to 40° to 100°C., passage of inert gas such as air and nitrogen gas therethrough, or treatment under a reduced pressure.

The sulfites in the system can be removed therefrom by converting them into free sulfur dioxide with mineral acids and then by treating the resulting mixture as mentioned above.

Alternatively, either sulfur dioxide or sulfites may be treated with a stoichiometric amount of oxidizing agents, for example iodine and hydrogen peroxide.

As is mentioned above, 2-chloroethylamine hydrochloride (m.p. 143° to 144°C.) is a preferred material for the preparation of sulfonylamides (I), but is so difficult to be isolated from the reaction mixture that the method can not be carried out industrially without overcoming the difficulty. One of the isolating methods would be separation of molten 2-chloroethylamine hydrochloride from the solvent by separation, however in this case heating the hydrochloride to above its melting point causes remarkable coloration of the system and thermal decomposition of the hydrochloride owing to its high melting point, thereby resulting in lowering of yield and purity of the hydrochloride. Another isolating method would be crystallization and filtration followed by drying of the hydrochloride. In this case, difficulty consists in selection of the material of a filter because the reaction mixture to be filtered contains corrosive hydrogen chloride and sulfur dioxide as a by-product in addition to organic solvents, and an extremely high deliquescence of the hydrochloride also makes difficult this isolating method. Moreover, drying after filtration requires a very expensive dryer because the hydrochloride to be dried contains hydrogen chloride and sulfur dioxide besides organic solvents. And, insufficient drying causes lowering of purity.

Therefore, the inventors have studied the isolation of the desired hydrochloride and developed a very effective method as mentioned below. As can easily be assumed to the skilled in the art, 2-chloroethylamine hydrochloride is considered to be very unstable in the presence of water, particularly at elevated temperatures and easily susceptible to hydrolysis, however the inventors, contrary to this conventional concept, have tried to extract the hydrochloride by adding water to the reaction mixture, and found that the hydrochloride is completely extracted with water at 15° to 90°C., preferably 40° to 80°C., surprisingly without the hydrolysis thereof. And the aqueous layer is not contaminated with organic solvents, so that the hydrochloride contains no impurities and recovery of organic solvent is quantitative. The amount of water used for extraction is 0.3 to 5 parts by weight based on 1 part by weight of the hydrochloride. The recovered organic solvents can be reused, as it is, for the next reaction.

Another method for the isolation of 2-chloro-ethylamine hydrochloride is a method which comprises chlorinating monoethanolamine hydrochloride with thionylchloride in a water-insoluble solvent which form an azeotropic mixture with water, adding water thereto, and then removing the solvent from the mixture by an azeotropic distillation to obtain the desired hydrochloride as an aqueous solution thereof. According to the method, the disadvantages above mentioned are completely overcome, and more surprisingly the desired product is not decomposed at all even under such a severe condition that the product is kept at a high temperature of the azeotropic distillation in the presence of water.

The solvents which are used herein include benzene, toluene, xylene, monochlorobenzene and 1,2-dichloroethane, and the amount thereof is preferably 0.5 to 10 parts by weight based on 1 part by weight of monoethanolamine hydrochloride. The amount of water added is 0.3 to 5 parts by weight based on 1 part by weight of 2-chloroethylamine hydrochloride. The distillation temperature is usually 70° to 120°C. The aqueous solution thus obtained can be used, as it is, for the subsequent reaction. The method is easy in the operation of each step and applicable to an industrial production.

Finally, in the course of experiments on the preparation of 2-chloroethylamine hydrochloride, it has been found that because the treatment of the by-products generated in the reaction, i.e. sulfur dioxide and hydrogen chloride, requires great expenditure, and because conversion of monoethanolamine into hydrochloride thereof requires considerable amount of hydrogen chloride, the reaction can not essentially be carried out industrially without overcoming the problems.

For overcoming these problems, it is considered that hydrogen chloride in a mixture with sulfur dioxide is used for preparing the salt of monoethanolamine. However, even if the mixture itself or approximately freed from sulfur dioxide is used for the salt-formation, sulfur dioxide which is present therein in amounts nearly equimolar to hydrogen chloride or in a trace amount reacts with monoethanolamine to produce bisulfite or sulfite thereby contaminating the reaction system and inhibiting the proceeding of the reaction, or to produce sulfamate which is also very undesirable for the reaction, as also suggested by Bogdanov (I. Gen. Chem. U.S.S.R., 17, 87, 1947).

Furthermore, even if hydrogen chloride having sulfur dioxide content of below several percent is used for the salt-formation, unknown products of amine type are produced in a certain amount and remarkably color the reaction system thereby giving an adverse effect on the quality of final product.

Thus, for making an effective use of the sulfur dioxide-containing hydrogen chloride as a material for salt-formation of ethanolamine, it must be made highly pure by removing sulfur dioxide completely therefrom. This is a serious disadvantage to an industrial application of the method.

The inventors have extensively studied an easy and effective use of sulfur dioxide-containing hydrogen chloride produced as a by-product, as a material for salt-formation of monoethanolamine, and found a very advantageous method in which the by-product containing hydrogen chloride and sulfur dioxide, a part of which sulfur dioxide may be removed in advance is contacted with monoethanolamine in the presence of water, to obtain monoethanolamine hydrochloride.

In the course of the chlorination under the conditions mentioned above, the by-product is generated in a gaseous mixture of hydrogen chloride and sulfur dioxide, and may be treated in advance to remove a part of sulfur dioxide.

In the present salt-formation, contact of water with sulfurdioxide-containing hydrogen chloride is very important. The contact can be achieved, for example, in such a way that the hydrogen chloride is passed through water to obtain an aqueous solution thereof and then the solution is added to a monoethanolamine solution in above-mentioned solvents to obtain monoethanolamine hydrochloride.

Alternatively the contact can be achieved by passing the hydrogen chloride through the monoethanol amine solution to which water is previously added.

The salt-formation proceeds quantitatively at a definite temperature, for example 10 to 100°C., during which sulfur dioxide of high purity is removed from the system. The amount of water added is 0.1 to 100 parts by weight, preferably 0.1 to 10 parts by weight based on 1 part by weight of monoethanolamine. The salt-formation requires hydrogen chloride in an equimolar amount to monoethanolamine, so that lack of the amount due to loss in operation must be supplemented.

Monoethanolamine hydrochloride thus obtained is equal in purity and yield to that obtained with usual hydrogen chloride or hydrochloric acid, and can be used for the chlorination with no difference between the two.

The present invention will be illustrated with reference to the following examples, which are only given for the purpose of illustration and not to be interpreted as limiting.

EXAMPLE 1

230 g. of ethylacetate were added to an aqueous solution of 116 g. (1 mole) of 2-chloroethylamine hydrochloride in 116 g. of water. 115 g. (1 mole) of methanesulfonylchloride was added dropwise to the mixture at 20 to 25°C. for 5 hours while stirring and adjusting pH to 7 to 9 with an aqueous solution of 80 g. (2 moles) of sodium hydroxide in 580 g. of water.

After the reaction was completed, the reaction mixture was separated into two layers and the organic layer was distilled under a reduced pressure to obtain 2-chloroethylmethanesulfonamide (b.p. 148° – 150°C./4 mmHg) in 84 % of yield.

According to the manner similar to that mentioned above, replacement of methanesulfonylchloride by each of ethane sulfonylchloride and n-propylsulfonylchloride gave the corresponding products in 75 to 86 % of yield.

The procedure mentioned above was repeated with one exception that the reaction was carried out at 15°±3°C. using potassium hydroxide in place of sodium hydroxide, whereby the similar result was obtained.

EXAMPLE 2

580 g. of methylisobutylketone were added to an aqueous solution of 116 g. (1 mole) of 2-chloroethylamino hydrochloride in 232 g. of water. 177 g. (1 mole) of benzenesulfonylchloride was added dropwise to the mixture at 25° to 30°C. for 3 hours while stirring and adjusting pH to 6.5 to 8.5 with an aqueous solution of 138 g. (1 mole) of potassium carbonate in 950 g. of water. The reaction mixture was treated in the same manner as described in Example 1 to obtain 2-chloroethyl-benzenesulfonylamide in 77 % of yield.

In the above example, replacement of benzene-sulfonylchloride by each of p-toluenesulfonylchloride, p-methoxybenzenesulfonylchloride, p-(N,N-dimethylamino)-benzenesulfonylchloride and m-nitrobenzene sulfonylchloride gave the corresponding products in any case in above 70 % of yield.

EXAMPLE 3

230 g. of 1,2-dichloroethane were added to an aqueous solution of 116 g. (1 mole) of 2-chloroethylamine hydrochloride in 200 g. of water. 115 g. (1 mole) of methanesulfonylchloride was added dropwise to the mixture at 15° to 20°C. for 5 hours while stirring and adjusting pH to 7 to 8 with an aqueous solution of 80 g. (2 moles) of sodium hydroxide in 160 g. of water.

After the reaction was completed, the reaction solution was separated into two layers, and the aqueous layer was extracted with 1,2-dichloroethane. The combined organic layer was distilled under a reduced pressure to obtain 2-chloroethylmethanesulfonamide (b.p. 148° – 150°C./4 mmHg) in 98 % of yield.

EXAMPLE 4

2-chloroethylmethanesulfonamide was obtained in 96 % of yield in completely the same manner as described in Example 3, except that chloroform was used as a solvent in place of 1,2-dichloroethane.

EXAMPLE 5

580 g. of monochlorobenzene were added to an aqueous solution of 116 g. (1 mole) of 2-chloroethylamine hydrochloride in 450 g. of water and 177 g. (1 mole) of benzenesulfonylchloride, and then the mixture was stirred at 10° ± 3°C. for 3 hours while adjusting pH to 6.5 to 8.5 with 138 g. (1 mole) of potassium carbonate. After completion of the reaction, the reaction solution was treated in the same manner as described in Example 3 to obtain 2-chloroethylbenzenesulfonamide in 94 % of yield.

EXAMPLE 6

2-chloroethylbenzenesulfonamide was obtained in 93 % of yield in completely the same manner as described in Example 5, except that monofluorobenzene was used as a solvent in place of monochlorobenzene.

COMPARATIVE EXAMPLES 1 – 6

2-chloroethylmethanesulfonamide was obtained in such a yield as shown in Table 1 in completely the same manner as described in Example 3, except that the reaction was carried out with solvents as shown in Table 1 or with no solvent.

Table 1

| Comparative example No. | Solvent | Yield (%) |
|---|---|---|
| 1 | benzene | 72 |
| 2 | toluene | 68 |
| 3 | ethylacetate | 82 |
| 4 | iso-butylalcohol | 65 |
| 5 | methyliso-butylketone | 77 |
| 6 | no solvent | 70 |

COMPARATIVE EXAMPLES 7 – 10

2-chloroethylbenzenesulfonamide was obtained in such a yield as shown in Table 2 in completely the same manner as described in Example 5, except that the reaction was carried out with solvents as shown in Table 2 or with no solvent.

Table 2

| Comparative example No. | Solvent | Yield (%) |
|---|---|---|
| 7 | n-hexane | 65 |
| 8 | cyclohexane | 65 |
| 9 | diethylether | 77 |
| 10 | no solvent | 64 |

EXAMPLE 7

A mixture of 975 g. of monoethanolamine hydrochloride, 3.7 g. of dimethylformamide and 3500 g. of benzene was heated to 75° to 80°C., and 1404 g. of thionylchloride were added dropwise thereto over 7 hours at the same temperature. After the addition was completed, the reaction solution was kept at the same temperature for further 1 hour and cooled to 30°C., and then 2900 g. of water was added thereto.

Then the solution was allowed to stand to separate into the benzene and aqueous layers. 4150 g. of the aqueous layer thus obtained contained 2-chloroethylamine hydrochloride which was produced in 98 % of yield, and 2.7 % by weight of free sulfur dioxide based on the aqueous layer.

EXAMPLE 8

423.5 g. of the aqueous solution (containing 1.0 mole of 2-chloroethylamine) which was obtained in Example 7 was heated to 70° to 75°C. and then nitrogen gas was passed therethrough for 3 hours. Then, the sulfur dioxide content of the solution was reduced to below 0.001 % by weight.

The aqueous solution from which sulfur dioxide had been removed was cooled to 5°C., and 423.5 g. of 1,2-dichloroethane and 200 g. of a 20 % aqueous sodium hydroxide solution were added thereto in this order. Then 57.3 g. (0.5 mole) of methanesulfonyl chloride were further added dropwise over 30 minutes.

Thereafter, the aqueous sodium hydroxide solution and the methanesulfonyl chloride were each added seven times in the same manner as described above, except that the amounts were each reduced each time to one half that of the preceding addition.

After the reaction was completed, the reaction solution was separated into the aqueous and dichloroethane layers, and the organic layer was distilled to recover 1,2-dichloroethane, and then further distilled to obtain 152.8 g. of 2-chloroethylmethanesulfonylamide (b.p. 148° – 150°C./4 mmHg) in 97 % of yield.

EXAMPLES 9 – 13

Methanesulfonylamides were obtained in the same manner as described in Example 7, except that sulfonylhalide of the formula (II) was replaced by those which were shown in Table 3. The results are as shown in Table 3.

into two layers. The separated lower layer was an aqueous mixture of 2-chloroethylamine hydrochloride, and it was found from analysis that the solution contained 114 g. of 2-chloro-ethylamine hydrochloride (yield 98 %).

In the above example, even in the case where the temperature at which water was added at the mixture was kept was 65° to 70°C., the result obtained was completely the same.

COMPARATIVE EXAMPLE 11

The reaction mixture obtained in the same manner as described in Example 18 was filtered at 80°C., and crystals obtained were dried at 90°C. The crystals, however, were difficult to dry to a constant weight due to their high hygroscopic property, and in addition a Table 3

| Example No. | R—SO$_2$—X X | R | Method for removing sulfur dioxide | Reaction temp. (°C.) | Product Chemical formula | Yield (%) |
|---|---|---|---|---|---|---|
| 9 | Cl | CH$_3$ | after neutralized with NaOH, iodine was added in amounts equivalent to SO$_2$ | 0 | CH$_3$SO$_2$NHC$_2$H$_4$Cl | 96 |
| 10 | Cl | CH$_3$ | kept at 60°C. and 300 mmHg for 30 minutes | 0 | CH$_3$SO$_2$NHC$_2$H$_4$Cl | 94 |
| 11 | Cl | –C$_6$H$_5$ | same as in Example 7 | 15 | C$_6$H$_5$SO$_2$NHC$_2$H$_4$Cl | 94 |
| 12 | Cl | C$_2$H$_5$ | same as in Example 7 | 10±3 | C$_2$H$_5$SO$_2$NHC$_2$H$_4$Cl | 93 |
| 13 | Cl | –C$_6$H$_4$–N(CH$_3$)$_2$ | same as in Example 7 | 45 | 4-(CH$_3$)$_2$NC$_6$H$_4$SO$_2$—NHC$_2$H$_4$Cl | 90 |

EXAMPLES 14 – 17

Methanesulfonylamides were obtained in the same manner as described in Examples 9-13, except that the aqueous solution of 2-chloroethylamine was used as it is without removing sulfur dioxide contained therein. The results are as shown in Table 4.

dryer made of stainless steel was much corroded by hydrogen chloride generated during drying. The yield was 95 %.

COMPARATIVE EXAMPLE 12

The reaction mixture obtained in the same manner as described in Example 18 was separated into two layers Table 4

| Example No. | X | R—SO$_2$—X R | Reaction temp. (°C.) | Product Chemical formula | Yield (%) | Corresponding example No. |
|---|---|---|---|---|---|---|
| 14 | Cl | CH$_3$ | 0 | CH$_3$SO$_2$NHC$_2$H$_4$Cl | 81 | 9, 10 |
| 15 | Cl | –C$_6$H$_5$ | 15 | C$_6$H$_5$SO$_2$NHC$_2$H$_4$Cl | 86 | 11 |
| 16 | Cl | C$_2$H$_5$ | 10±3 | C$_2$H$_5$SO$_2$NHC$_2$H$_4$Cl | 82 | 12 |
| 17 | Cl | –C$_6$H$_4$–N(CH$_3$)$_2$ | 45 | 4-(CH$_3$)$_2$NC$_6$H$_4$—SO$_2$NHC$_2$H$_4$Cl | 84 | 13 |

EXAMPLE 18

A mixture of 97.5 g. (1.0 mole) of monoethanolamine hydrochloride and 190 g. of xylene was heated to 70°C., and 124 g. of thionylchloride were added dropwise at 70° to 80°C. over 3 hours. Thereafter, the mixture was kept at the same temperature for further two hours, then cooled to 45°C. at which 100 g. of water were added thereto. After stirring for 30 minutes, the reaction solution was allowed to stand to separate at 143°C. Both the lower layer of molten desired product and the upper xylene layer were remarkably colored. The yield was 93 %, and both the yield and purity were lower than in the above examples.

EXAMPLE 19

A mixture of 62 g. of ethanolamine and 190 g. of xylene was heated to 50°C., at which 102 g. of a 35 % hydrochloric acid were added thereto. The mixture was kept at 95°C. during which most of water was recovered, and then the mixture was heated to 138°C. and kept at the same temperature for 30 minutes. The recovery of water was above 98 %. Xylene which had been distilled off was separated from water and returned to the system. Next, the reaction system was cooled to 75°C. and 124 g. thionylchloride were added dropwise at 70° to 75°C. over 3 hours, thereafter the system was kept at the same temperature for further 3 hours. 100 g. of water were added to the system which was then heated to distill off xylene from the system. The final temperature of the system was 110°C. The distilled water was separated from xylene and returned to the system. The recovery of xylene was above 97 %. The xylene could be reused for the next reaction. Thus, 214 g. of a clear aqueous solution of 2-chloroethylamine containing 53 % of 2-chloroethylamine was obtained (yield 98 %).

In the above example, completely the same result was obtained even in the case where ethanolamine and 35 % hydrochloric acid were replaced by a 48 % aqueous ethanolamine solution and recovered hydrogen chloride or hydrochloric acid containing sulfur dioxide, respectively.

COMPARATIVE EXAMPLE 13 (treatment after chlorination)

The reaction mixture after chlorination obtained in the same manner as described in Example 19 was filtered at 80°C., and then dried at about 90°C. The crystallites obtained were so hygroscopic that they were difficult to dry to a constant weight, and in addition, hydrogen chloride generated during drying made the operation very difficult. The yield was 95 %.

COMPARATIVE EXAMPLE 14 (treatment after chlorination)

The reaction mixture after chlorination obtained in the same manner as described in Example 19 was separated into two layers at 143° to 150°C. Both the lower layer of molten desired product and the upper xylene layer were remarkably colored. The yield was 93 %, and both the yield and purity were lower than in the above examples.

COMPARATIVE EXAMPLE 15

62 g. of monoethanolamine were heated to 40°C., and sulfurdioxide-containing hydrogen chloride which was recovered in Example 19 was passed therethrough in a proportion of 1.1:1 by molar ratio of monoethanolamine to hydrogen chloride. The reaction system became black brown. Thereafter chlorination was carried out in the same manner as described in Example 19 to obtain a muddy product containing black brown 2-chloroethylamine hydrochloride. The yield was 35 %.

EXAMPLE 20

A mixture of 97.5 g. of monoethanolamine hydrochloride, 130 g. of benzene and 0.8 g. of N,N-dimethylformamide was heated to 80°C. at which 136.9 g. of thionyl-chloride were added dropwise over 3 hours, and then the reaction solution was maintained at the same temperature for 1 hour. After the reaction was completed, the solution was treated in a usual manner to obtain 112.6 g. of 2-chloroethylamine hydrochloride (yield 97 %).

During the reaction, a mixture of sulfur dioxide and hydrogen chloride which was produced as a by-product was passed at 40°C. through a mixed solution of 61.1 g. of monoethanolamine, 130 g. of benzene and 61.1 g. of water. Thus, at the same time with completion of the above-mentioned chlorination, 97 % of monoethanolamine was converted into its hydrochloride. To convert the remaining monoethanolamine into its hydrochloride, 6.3 g. of a 35 % hydrochloric acid were additionally added.

The mixed solution thus obtained containing monoethanolamine hydrochloride, water and benzene was subjected to an azeotropic distillation to remove water in such a way that the distillate was separated into water and benzene, benzene only being returned to the system. Thus a mixture of monoethanolamine hydrochloride and benzene was obtained. The hydrochloride was essentially colorless and clear even in the molten state.

The mixture thus obtained was chlorinated with thionylchloride in the same manner as described above to obtain 113.1 g. of 2-chloroethylamine hydrochloride (yield 97.5 %).

According to the above process, 41.3 g. (yield 86 %) of sulfur dioxide containing essentially no hydrogen chloride were obtained out of the system.

COMPARATIVE EXAMPLE 16

In Example 20, a mixture of sulfur dioxide and hydrogen chloride which was produced as a by-product was passed through a monoethanolamine-benzene mixed solution containing no water. The hydrochloride thus obtained was colored dark brown in a molten state, and the degree of coloration was about 13 according to the Gardner Scale. The hydrochloride was chlorinated in the same manner as described in Example 20 to obtain deep brown 2-chloroethylamine hydrochloride.

EXAMPLE 21

At the second stage of Example 20, 113.1 g. of water were added at 50° to 55°C. to 2-chloroethylamine hydrochloride which had been obtained using hydrogen chloride produced as a by-product. Then the mixture was heated to distill off benzene as a water azeotrope, from which water was separated and returned to the system. The boiling point of the system was about 70°C. When the system was heated to about 108°C., benzene was completely removed from the system. The aqueous solution of 2-chloroethylamine hydrochloride thus obtained was 225.0 g. and contained no sulfur dioxide at all.

300 g. of chloroform were added to the aqueous solution and kept at 20°C. Then, to the mixture were added 300 g. of a 10 % aqueous sodium hydroxide solution and 112.1 g. of methanesulfonylamide at 20°±2°C. over 3 hours while adjusting pH to 7 to 8.5, and the mixture was maintained for 1 hour under the same condition. After the reaction was completed, the separated aqueous layer was reextracted with 100 g. of chloroform, then combined chloroform layer was freed from chloroform by distillation to obtain 150.6 g. of 2-chloroethylmethanesulfonylamide. The over-all yield was 95.5 %.

EXAMPLE 22

2-chloroethylamine hydrochloride was prepared, using hydrogen chloride produced as a by-product, in the same manner as described in the first stage of Example 20 except that benzene was replaced by the same amount of xylene. After 113.1 g. of water were added at 50°C. to the system thus obtained, the system was stirred at the same temperature for 30 minutes, and then separated into two layers. The aqueous layer was 226 g. and its sulfur dioxide content was 1.8 %. The layer was treated in the same manner as described in Example 8 to reduce the sulfur dixoide content to below 0.01 %. The aqueous solution thus obtained was 224.5 g. 230 g. of 1,2-dichloroethane were added to the solution and then treated in the same manner as described in Example 3 to obtain 149 g. of 2-chloroethyl-methanesulfonylamide.

EXAMPLE 23

214 g. of the aqueous solution of 2-chloroethylamine obtained in Example 19 were reacted in the same manner as described in Example 5 to obtain 2-chloroethyl-benzenesulfonylamide in 91 % of yield.

EXAMPLE 24

124 g. of the aqueous solution of 2-chloroethylamine obtained in Example 18 was treated in the same manner as described in Example 7 to obtain the aqueous solution containing no sulfur dioxide. The solution thus obtained was subjected to condensation reaction as described in Example 3 to obtain 2-chloroethylmethanesulfonylamide in 93.6 % of yield.

What we claim is:

1. A method for preparing a sulfonylamide of the formula,

wherein R is a $C_1 - C_6$ alkyl group, phenyl or phenyl substituted by a member selected from the group consisting of halogen, $C_1 - C_6$ alkyl, $C_1 - c_3$ alkoxy, acetyl, $C_1 - C_2$ acylamino, $C_1 - C_2$ alkyl amino or nitro, which comprises reacting a sulfonylhalide of the formula,

wherein R is the same as defined above and X is a chlorine or bromine atom, with 2-chloroethylamine or a salt thereof in the presence of a base in a halogenated hydrocarbon solvent at a temperature of 0° to 80°C. and at a pH of 5 to 10.

2. The method according to claim 1, wherein the base is an alkali hydroxide or an alkali carbonate or bicarbonate.

3. The method according to claim 1, wherein the molar ratio of the sulfonylhalide to 2-chloroethylamine or its salt is about 1:1.

4. The method according to claim 1, wherein the solvent is chloroform, carbon tetrachloride 1,2-dichloro-ethane, 1,1,2-trichloroethane, 1,1,2,2-tetrachloroethane, 1,2-dichloroethylene, 1,1,2-trichloroethylene, 1,1,2,2-tetrachloroethylene, n-propyl chloride, 1,2-difluoro-1,1,2,2-tetrachloroethane, monochlorobenzene, o-dichloro-benzene, dichlorobenzenes or fluorobenzene.

5. The method according to claim 1, wherein the salt of 2-chloroethylamine is a sulfate, hydrochloride, hydrobromide or acetate of 2-chloroethylamine.

6. The method according to claim 5, wherein the 2-chloroethylaminehydrochloride is prepared by chlorinating monoethanolamine hydrochloride with thionyl chloride and removing sulfur dioxide or sulfites contained in the chlorination mixture.

7. The method according to claim 5, wherein the 2-chloroethylamine hydrochloride is prepared in the form of an aqueous solution by carrying out the chlorination in the presence of a water-insoluble solvent capable of forming a water azeotrope, adding water to the reaction mixture, and then removing the solvent from the reaction mixture as a water azeotrope.

8. The method according to claim 7, wherein the said monoethanolamine hydrochloride is prepared by reacting ethanolamine in the presence of water, with a mixture of hydrogen chloride with sulfur dioxide, which mixture is produced as a by-product during the chlorination.

9. The method according to claim 6 wherein the chlorinating is conducted in a water-insoluble solvent, and the removal is conducted by extraction using water to obtain the 2-chloroethylamine hydrochloride in the form of an aqueous solution.

10. A method for preparing a sulfonylamide of the formula $R-SO_2NHC_2H_4Cl$ wherein R is a $C_1 - C_6$ alkyl group, phenyl or phenyl substituted by a member selected from the group consisting of halogen, $C_1 - C_6$ alkyl, $C_1 - C_3$ alkoxy, acetyl, $C_1 - c_2$ acylamino, $C_1 - C_2$ alkyl amino or nitro, which comprises the steps (1) reacting monoethanolamine hydrochloride with thionyl chloride in a waterinsoluble solvent, (2) removing sulfur dioxide or sulfites contained in the reaction mixture of the step (1) by extraction with water or distillation to obtain 2-chloroethylamine hydrochloride in the form of an aqueous solution, and then (3) reacting the 2-chloroethylamine hydrochloride in the form of an aqueous solution with a sulfonyl halide of the formula $R-SO_2-X$ wherein R is as defined above and X is a chlorine or bromine atom or a salt thereof in the presence of a base in a halogenated hydrocarbon solvent at a temperature of 0° to 80°C. and at a pH of 5 to 10.

* * * * *